US012087435B2

(12) United States Patent
Fujikake

(10) Patent No.: US 12,087,435 B2
(45) Date of Patent: Sep. 10, 2024

(54) MAINTENANCE SYSTEM, MAINTENANCE METHOD, AND PROGRAM

(71) Applicant: TOYOTA JIDOSHA KABUSHIKI KAISHA, Toyota (JP)

(72) Inventor: Yoshinori Fujikake, Nagakute (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 682 days.

(21) Appl. No.: 17/224,619

(22) Filed: Apr. 7, 2021

(65) Prior Publication Data
US 2021/0358607 A1 Nov. 18, 2021

(30) Foreign Application Priority Data
May 15, 2020 (JP) .................... 2020-086051

(51) Int. Cl.
*G16H 40/40* (2018.01)
*A61H 3/00* (2006.01)
*G16H 20/30* (2018.01)

(52) U.S. Cl.
CPC .............. *G16H 40/40* (2018.01); *A61H 3/00* (2013.01); *G16H 20/30* (2018.01);
(Continued)

(58) Field of Classification Search
CPC ............ A61H 3/00; A61H 2003/007; A61H 2201/164; A61H 2201/1671;
(Continued)

(56) References Cited

U.S. PATENT DOCUMENTS 10,881,911 B2 * 1/2021 Kwon ................ A63B 69/0064
2006/0205566 A1 * 9/2006 Watterson ......... H04L 12/40045
482/902
(Continued)

FOREIGN PATENT DOCUMENTS

JP 2018-34235 A 3/2018
JP 2018-034236 A 3/2018
(Continued)

*Primary Examiner* — Tu A Vo
*Assistant Examiner* — Kelsey E Baller
(74) *Attorney, Agent, or Firm* — Oliff PLC

(57) ABSTRACT

A maintenance system includes: a walking training apparatus including a walking assistance apparatus attached to a leg of a trainee, and to assist the trainee in walking, and first transmission means for transmitting information in which information about the number of times of walking or a time of walking performed in the walking assistance apparatus is associated with a component of the walking assistance apparatus; and a server including determination means for comparing the information about the number of times of the walking or the time of the walking transmitted from the first transmission means with a preset evaluation value for durability of the walking assistance apparatus, and determining a timing for performing maintenance for the walking assistance apparatus, and second transmission means for transmitting maintenance information including the timing of the maintenance determined by the determination means and information about the associated component of the walking assistance apparatus.

6 Claims, 10 Drawing Sheets

(52) U.S. Cl.
CPC .. *A61H 2003/007* (2013.01); *A61H 2201/164* (2013.01); *A61H 2201/1671* (2013.01)

(58) Field of Classification Search
CPC .... A61H 2201/5007; A61H 2201/1642; A61H 2201/5092; A61H 2201/1261; A61H 2201/165; A61H 2201/5061; A61H 1/0262; A61H 1/0266; A61H 2205/10; G16H 40/40; G16H 20/30; A61B 5/1118; A63B 22/02
See application file for complete search history.

(56) References Cited

U.S. PATENT DOCUMENTS

| | | | |
|---|---|---|---|
| 2011/0071442 A1* | 3/2011 | Park | A61B 5/112 |
| | | | 601/35 |
| 2012/0116550 A1* | 5/2012 | Hoffman | A61B 5/6898 |
| | | | 700/91 |
| 2017/0049660 A1* | 2/2017 | Sugata | A61B 5/1038 |
| 2017/0128769 A1* | 5/2017 | Long | H04L 67/10 |
| 2018/0289523 A1 | 10/2018 | Fujikake et al. | |

FOREIGN PATENT DOCUMENTS

| | | |
|---|---|---|
| JP | 2018-135974 A | 8/2018 |
| JP | 2018-175316 A | 11/2018 |
| JP | 6554996 B2 | 8/2019 |

\* cited by examiner

MAINTENANCE SYSTEM, MAINTENANCE METHOD, AND PROGRAM

CROSS REFERENCE TO RELATED APPLICATIONS

This application is based upon and claims the benefit of priority from Japanese patent application No. 2020-086051, filed on May 15, 2020, the disclosure of which is incorporated herein in its entirety by reference.

BACKGROUND

The present disclosure relates to a maintenance system, a maintenance method, and a program.

A walking training apparatus including a walking assistance apparatus which is attached to a leg of a user and assists the user in walking has been known (see, for example, Japanese Patent No. 6554996).

SUMMARY

As the user performs walking training, the walking assistance apparatus repeatedly receives loads (i.e., pressures) from the leg of the user because of the walking. Because of these loads caused by the walking, each of the components constituting the walking assistance apparatus is worn and eventually requires maintenance. Therefore, it has been desired to develop a maintenance system capable of presenting an appropriate maintenance timing that is not too early and not too late.

The present disclosure has been made to solve the above-described problem and an object thereof is to provide a maintenance system, a maintenance method, and a program capable of presenting an appropriate maintenance timing.

A first exemplary aspect is a maintenance system including:

a walking training apparatus including:

a walking assistance apparatus configured to be attached to a leg of a trainee, and to assist the trainee in walking; and first transmission means for transmitting information in which information about the number of times of walking or a time of walking performed in the walking assistance apparatus is associated with a component of the walking assistance apparatus; and a server including:

determination means for comparing the information about the number of times of the walking or the time of the walking transmitted from the first transmission means with a preset evaluation value for durability of the walking assistance apparatus, and determining a timing for performing maintenance for the walking assistance apparatus; and second transmission means for transmitting maintenance information including the timing of the maintenance determined by the determination means and information about the associated component of the walking assistance apparatus, the associated component being an object to be maintained.

In this aspect, the walking assistance apparatus may calculate a moment load around an ankle joint part of the walking assistance apparatus, and calculate an integrated value obtained by integrating the calculated moment load and the number of times of the walking or the time of the walking performed in the walking assistance apparatus; the first transmission means may transmit, as information about the number of times of the walking or the time of the walking, the calculated integrated value while associating the calculated integrated value with the component of the walking assistance apparatus; and the determination means may compare the integrated value transmitted from the first transmission means with the preset evaluation value for the durability of the walking assistance apparatus, and determine the timing for performing the maintenance for the walking assistance apparatus.

In this aspect, the walking assistance apparatus may include a thigh frame, a lower-leg frame connected to the thigh frame through a knee joint part, a sole frame connected to the lower-leg frame through an ankle joint part, a motor unit configured to rotationally drive the knee joint part, and an adjustment mechanism configured to adjust a movable range of the ankle joint part; and the component of the walking assistance apparatus may be a component configured to restrict the movable range of the ankle joint part in the adjustment mechanism.

In this aspect, the server may further include changing means for changing the evaluation value for the durability of the walking assistance apparatus.

In this aspect, the first transmission means may transmit, to the server, information about at least one of a skeletal movement of the trainee, a center of a load exerted on the sole, and a knee joint angle detected by a sensor provided in the walking training apparatus together with the information in which the information about the number of times of the walking or the time of the walking is associated with the component of the walking assistance apparatus; the server may further include bias determination means for determining a direction of a bias of the load in the walking of the trainee based on the information about at least one of the skeletal movement of the trainee, the center of the load exerted on the sole, and the knee joint angle transmitted from the first transmission means; the evaluation value for the durability may be set according to the direction of the bias of the load; and the determination means may set the evaluation value for the durability according to the direction of the bias of the load in the walking of the trainee determined by the bias determination means, compare the set evaluation value for the durability with the information about the number of times of the walking or the time transmitted from the first transmission means, and determine the timing for performing the maintenance for the walking assistance apparatus.

Another exemplary aspect may be a maintenance method including:

transmitting, to a server, information in which information about the number of times of walking or a time of walking performed in a walking assistance apparatus is associated with a component of the walking assistance apparatus, the walking assistance apparatus being configured to be attached to a leg of a trainee, and to assist the trainee in walking;

comparing, by the server, the transmitted information about the number of times of the walking or the time of the walking with a preset evaluation value for durability of the walking assistance apparatus, and determining a timing for performing maintenance for the walking assistance apparatus; and transmitting, by the server, maintenance information including the determined timing of the maintenance and information about the associated component of the walking assistance apparatus, the associated component being an object to be maintained.

Another exemplary aspect may be a program for causing a computer to perform:

a process for transmitting, to a server, information in which information about the number of times of walking or a time of walking performed in a walking assistance apparatus is associated with a component of the walking assistance apparatus, the walking assistance apparatus being configured to be attached to a leg of a trainee, and to assist the trainee in walking;

a process for comparing, by the server, the transmitted information about the number of times of the walking or the time of the walking with a preset evaluation value for durability of the walking assistance apparatus, and determining a timing for performing maintenance for the walking assistance apparatus; and a process for transmitting, by the server, maintenance information including the determined timing of the maintenance and information about the associated component of the walking assistance apparatus, the associated component being an object to be maintained.

According to the present disclosure, it is possible to provide a maintenance system, a maintenance method, and a program capable of presenting an appropriate maintenance timing.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

First Embodiment

Figure 1:
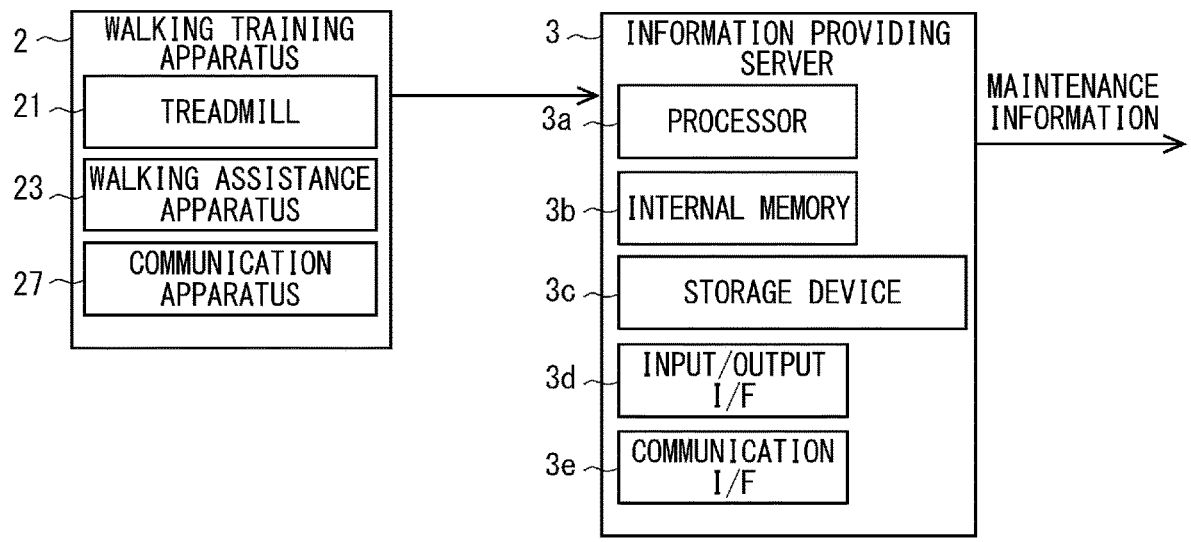
FIG. 1 is a block diagram showing a schematic system configuration of a maintenance system according to an embodiment.

Embodiments according to the present disclosure will be described hereinafter with reference to the drawings. FIG. 1 is a block diagram showing a schematic system configuration of a maintenance system according to an embodiment.

A maintenance system 1 according to this embodiment includes a walking training apparatus 2 by which a trainee performs walking training, and an information providing server 3 which provides maintenance information.

Figure 2:
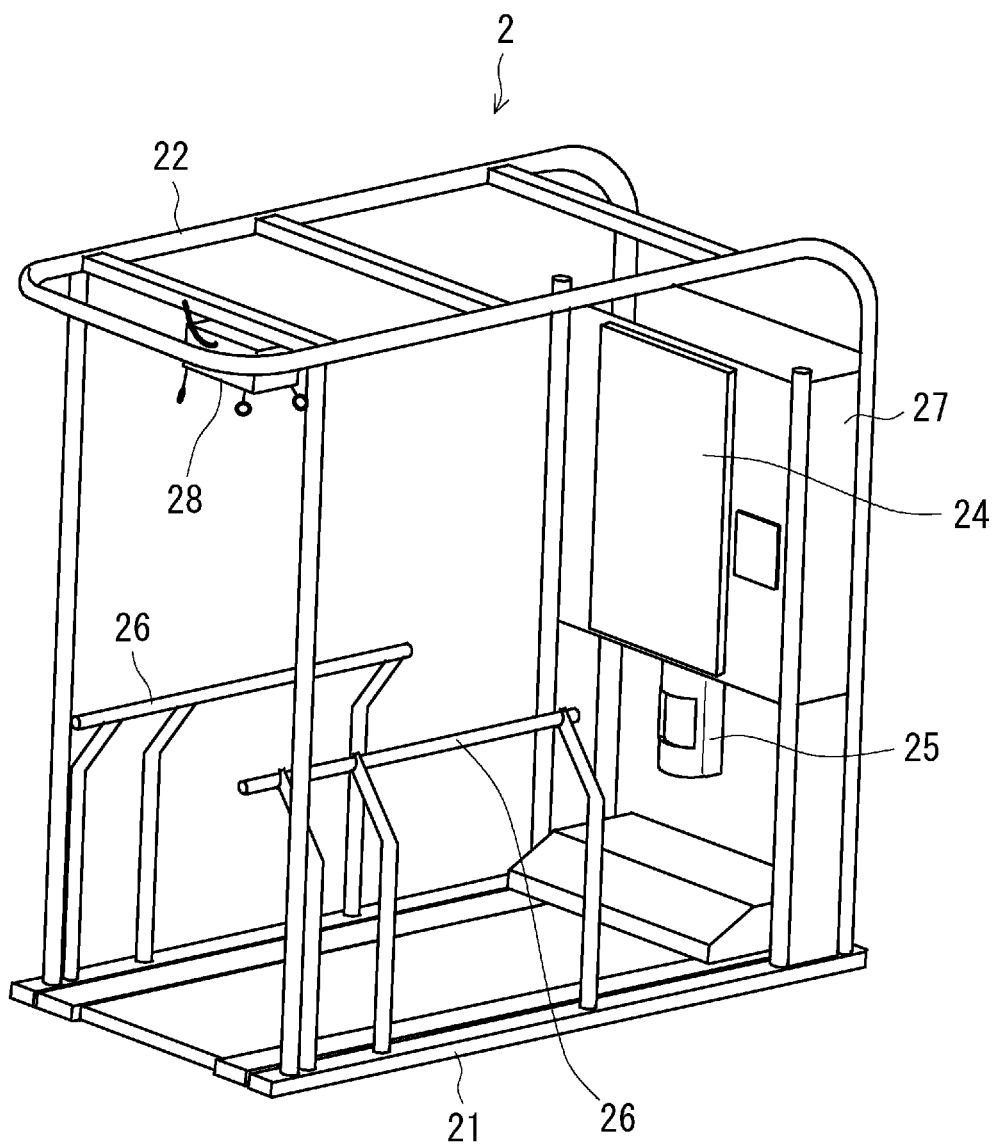
FIG. 2 is a perspective view showing a schematic configuration of a walking training apparatus according to an embodiment.

FIG. 2 is a perspective view showing a schematic configuration of the walking training apparatus according to this embodiment. The walking training apparatus 2 is provided in a hospital or a rehabilitation facility. The walking training apparatus 2 includes a treadmill 21, a frame main body 22, a walking assistance apparatus 23, and the like. The treadmill 21 rotates a ring-shaped belt. A trainee performs walking training by getting on the belt and performing walking according to the movement of the belt.

The frame main body 22 is composed of a plurality of frames connected above the treadmill 21. In the frame main body 22, a pulling machine 28 that pulls the trainee upward and thereby assists him/her, a monitor 24 that displays various information items, a sensor(s) 25 that detects a walking state of the trainee, handrails 26 that the trainee grasps during the training, a communication apparatus 27 that transmits/receives data, and the like are provided.

The monitor 24 displays information about, for example, training instructions, a training menu, and training information (such as a walking speed and biological information). The sensor 25 is, for example, a 3D (three dimensional) sensor capable of detecting the skeletal movement of the trainee. The 3D sensor acquires a depth image showing projections and depressions on the body surface of the person (e.g., the trainee) by irradiating the body surface with laser light, and recognizes the skeletal structure of the person by extracting 3D coordinates of joints from the depth image. The sensor 25 transmits the detected skeletal movement of the trainee to the communication apparatus 27.

The communication apparatus 27 is a specific example of the first transmission means. The communication apparatus 27 is connected to the walking assistance apparatus 23 through wireless communication such as Bluetooth (Registered Trademark) or Wifi (Registered Trademark), or through wired communication. The communication apparatus 27 can transmit/receive data to/from the walking assistance apparatus 23. Further, the communication apparatus 27 can transmit/receive data to/from the information providing server 3 through a communication network such as the Internet. Note that the communication apparatus 27 may be disposed in the walking assistance apparatus 23.

The communication apparatus 27 transmits information in which information about the number of times of walking performed by the walking assistance apparatus 23 is associated with a component of the walking assistance apparatus 23, which has been received from the walking assistance apparatus 23. Note that the walking training apparatus 2 does not necessarily have to include the treadmill 21 and the frame main body 22.

Figure 3:
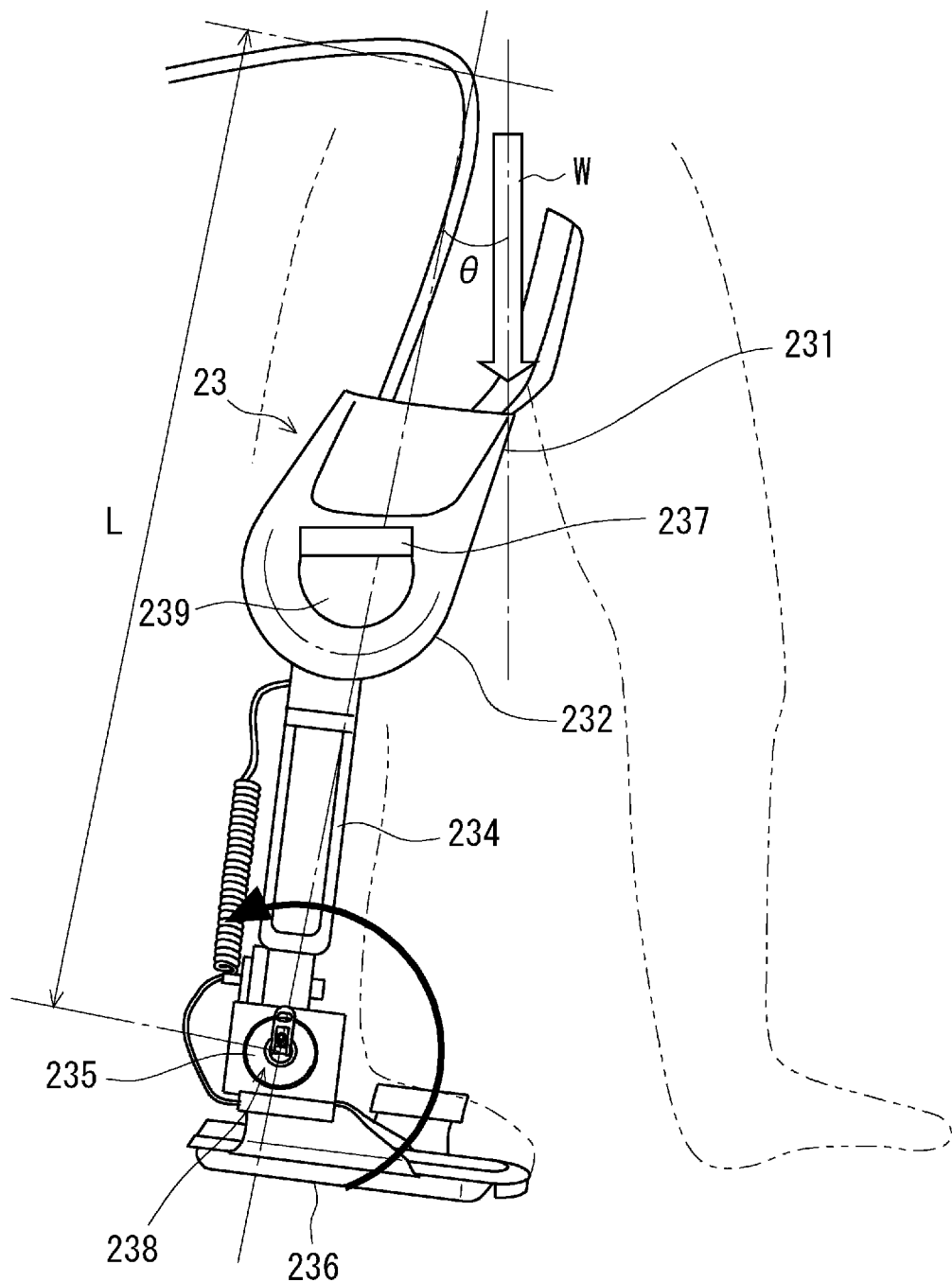
FIG. 3 is a side view showing a schematic configuration of a walking assistance apparatus according to an embodiment.

FIG. 3 is a side view showing a schematic configuration of the walking assistance apparatus according to this embodiment. The walking assistance apparatus 23 is attached to a leg of a trainee and assists the trainee in walking. The walking assistance apparatus 23 includes a thigh frame 231, a lower-leg frame 234 connected to the thigh frame 231 through a knee joint part 232, a sole frame 236 connected to the lower-leg frame 234 through an ankle joint part 235, a motor unit 237 that rotationally drive the knee joint part 232, and an adjustment mechanism 238 that adjusts the movable range of the ankle joint part 235.

An angle sensor 239 that detects the angle of the knee joint part 232 is provided in the knee joint part 232. Note that the above-described configuration of the walking assistance apparatus 23 is merely an example, and its configuration is not limited to this example. For example, the walking assistance apparatus 23 may include a motor unit that rotationally drives the ankle joint part 235.

Figure 4:
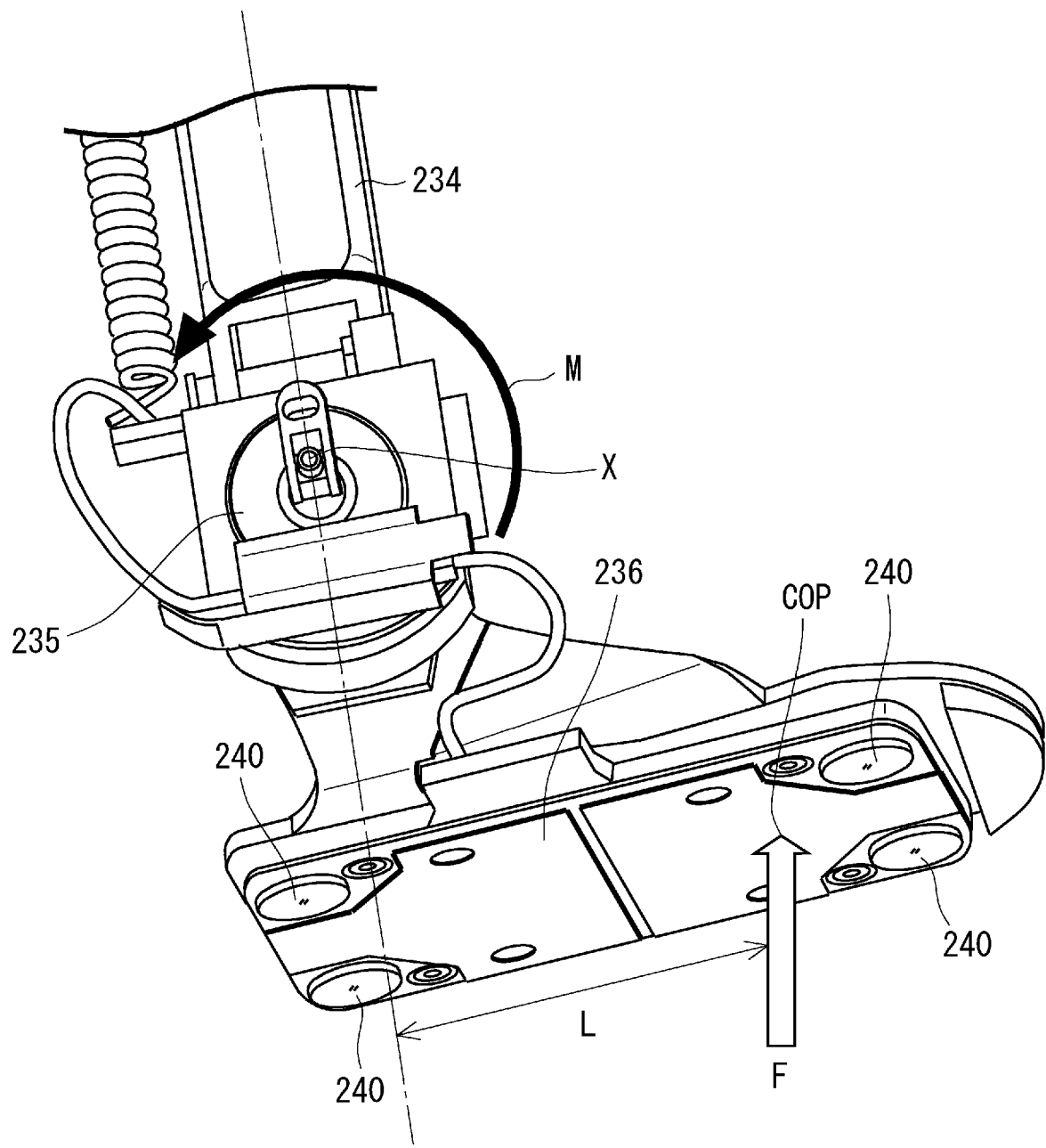
FIG. 4 is a perspective view showing a schematic configuration of a sole frame according to an embodiment.

FIG. 4 is a perspective view showing a schematic configuration of the sole frame. In the sole frame 236, a pair of load sensors 240 is provided on each of the toe side and the heel side on the sole surface. Each of the load sensors 240 is, for example, a vertical load sensor that detects a load (i.e., a pressure) exerted in a direction perpendicular to the sole of the sole frame 236. Note that the number and positions of the load sensors 240 provided in the sole frame 236 may be arbitrarily determined.

The walking assistance apparatus 23 calculates the position of the center of the load (COP: Center of Pressure) exerted on the sole (hereinafter referred to as the COP position) during the gait motion performed by the trainee based on the load detected by the load sensors 240.

For example, the center position on the sole of the sole frame 236 is defined as the origin of a 2D (two dimensional) XY-coordinate system. Then, the position of a first load sensor 240 on the toe side is expressed as (x1, y1), and the position of a second load sensor 240 on the toe side is expressed as (x2, y2). Further, the position of a third load sensor 240 on the heel side is expressed as (x3, y3), and the position of a fourth load sensor 240 on the heel side is expressed as (x4, y4). The amount of a load exerted on each of the load sensors 240 is represented by Ni (i=1 to 4). The walking assistance apparatus 23 calculates the COP position ($x_{COP}$, $y_{COP}$) by using, for example, the below-shown expressions.

$$x_{COP} = \frac{\sum_{i=1}^{4} N_i x_i}{\sum_{i=1}^{4} N_i} \quad \text{[Expression 1]}$$

$$y_{COP} = \frac{\sum_{i=1}^{4} N_i y_i}{\sum_{i=1}^{4} N_i}$$

The above-described method for calculating a COP position is merely an example, and the method is not limited to this example. For example, instead of using the load sensors 240, a load distribution sensor that detects a distribution of loads (i.e., pressures) on the sole may be provided on the sole of the sole frame 236. The walking assistance apparatus 23 may calculate the COP position based on the distribution of loads on the sole detected by the load distribution sensor.

The walking assistance apparatus 23 calculates a dorsiflex moment load around the ankle joint part 235 based on the loads detected by the respective load sensors 240 and the COP position. For example, the walking assistance apparatus 23 calculates a sole load F at the COP position based on the loads detected by the respective load sensors 240. The walking assistance apparatus 23 calculates a distance L from the ankle joint axis X to the COP position. The walking assistance apparatus 23 calculates the dorsiflex moment load M around the ankle joint part 235 by integrating the sole load F and the distance L.

Dorsiflex moment load M (Nm)=Sole load F (N) at COP Position×Distance L (m) from Ankle joint axis X to COP Position The COP position changes with time. Therefore, as the dorsiflex moment load M, a maximum value thereof in each step, for example, may be used.

Note that the walking assistance apparatus 23 may calculate the dorsiflex moment load M around the ankle joint part 235 based on the below-shown expression.

Dorsiflex moment load M (Nm)=Weight W (N) of Trainee×Distance L (m) from Ankle joint part 235 to Center of gravity×sin θ

The angle θ is an inclination angle (rad) of the thigh part, and is calculated based on the angle of the knee joint part 232 detected by the angle sensor 239. A value that is statistically converted (calculated) from the height of the trainee may be set to the distance L from the ankle joint part 235 to the center of gravity.

The walking assistance apparatus 23 calculates the number N of times of walking performed in the walking assistance apparatus 23 based on the loads on the sole detected by the respective load sensors 240. The walking assistance apparatus 23 calculates an integrated value MN obtained by integrating the calculated dorsiflex moment load M around the ankle joint part 235 and the number N of times of walking. The walking assistance apparatus 23 associates the calculated integrated value, as information about the number of times of walking, with a component of the walking assistance apparatus 23, and transmits the associated information to the communication apparatus 27.

Note that the walking assistance apparatus 23 calculates an integrated value obtained by integrating the dorsiflex moment load around the ankle joint part 235 and the number of times of walking, associates the calculated integrated value of the number of times of walking, as information about the number of times of walking, with a component of the walking assistance apparatus 23, and transmits the associated information to the communication apparatus 27. However, the operations of the walking assistance apparatus 23 are not limited to these operations.

The walking assistance apparatus 23 may calculate an integral value obtained by integrating the dorsiflex moment load around the ankle joint part 235 with respect to the time of walking, associate the calculated integral value, as information about the time of walking, with a component of the walking assistance apparatus 23, and transmit the associated information to the communication apparatus 27.

The cumulative value of the dorsiflex moment load around the ankle joint part 235 caused by a walking training is roughly proportional to the time of the walking as well as to the number of times of the walking. Therefore, it is possible to obtain an integrated value for the time of the walking as well as for the number of times of the walking.

The above-described associated component of the walking assistance apparatus 23 is set in advance in the walking assistance apparatus 23, and a user can change the set component through an input device or the like. The above-described associated component of the walking assistance apparatus 23 is, for example, a consumable component that is consumed due to walking performed in the walking assistance apparatus 23 or a sensor that requires a calibration.

Figure 5:
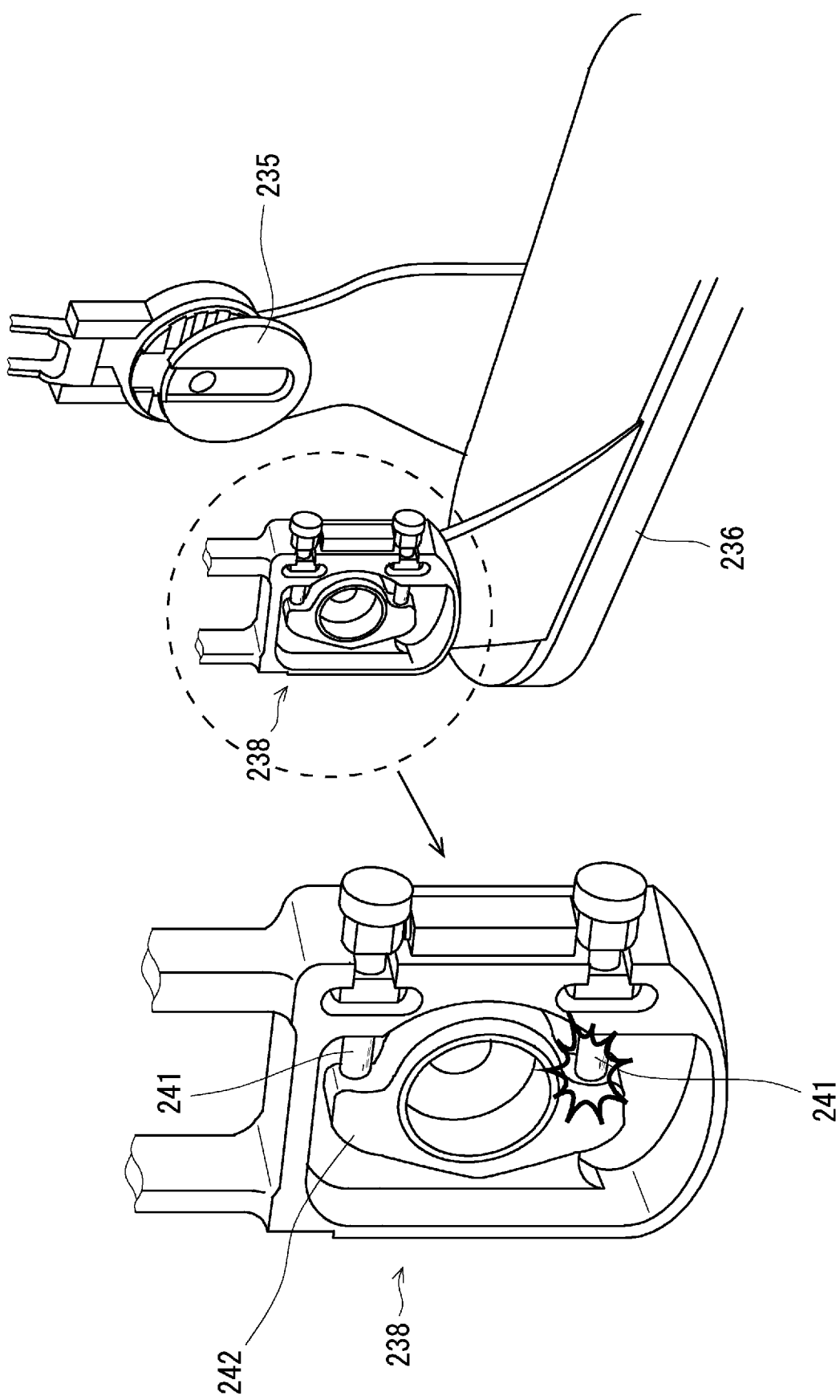
FIG. 5 is an enlarged view of an adjustment mechanism of a walking assistance apparatus.

For example, the sensor may be the load sensor(s) 240 or the like. The consumable component is a stopper pin 241 and/or a stopper shaft 242 of the adjustment mechanism 238 (which will be described below). FIG. 5 is an enlarged view of the adjustment mechanism of the walking assistance apparatus. As shown in FIG. 5, in the adjustment mechanism 238, the range of planter-flexion and dorsiflex movements of the ankle joint part 235 is restricted by a pair of stopper pins 241 and a stopper shaft 242.

It should be noted that as a user performs walking training, the walking assistance apparatus 23 repeatedly receives loads (i.e., pressures) from the leg of the user because of the walking. Because of these loads caused by the walking, each of the components constituting the walking assistance apparatus 23 is worn and eventually requires maintenance.

For example, the trunk (the torso) of a patient is unstable in the early stage of rehabilitation. Therefore, in many cases, the range of planter-flexion and dorsiflex movements of the ankle joint part 235 is restricted by the stopper pins 241 and the stopper shaft 242 of the adjustment mechanism 238. Further, during the actual walking training, the dorsiflex moment load around the ankle joint part 235 could reach 70 Nm at maximum (when the patient kicks out the ground), and the load exerted at the tip of the stopper pin 241 could reach about 3,500 N. This dorsiflex moment load occurs at each step and advances (i.e., increases) the wear of the stopper pins 241 and the stopper shaft 242.

The stopper pins 241 and the stopper shaft 242 are worn as described above, and the rattle thereof around the ankle joint part 235 increases. Therefore, the walking performed in the walking assistance apparatus 23 becomes unstable, and the walking assistance apparatus 23 requires early maintenance.

It should be noted that in the case in which the timing of such maintenance is set, if the maintenance period is set to a long span, the walking assistance apparatus, which is in the unstable state as described above, is left unattended for a certain period. On the other hand, if the maintenance period is set to a short span, the walking assistance apparatus is frequently stopped for the maintenance, so that the efficiency of the rehabilitation operation is lowered.

Therefore, it has been strongly desired to develop a maintenance system capable of presenting an appropriate maintenance timing that is not too early and not too late. To this end, the maintenance system 1 according to this embodiment includes the information providing server 3 that provides maintenance information including a timing for performing maintenance for the walking assistance apparatus 23 to a maintenance company or the like.

As a result, the maintenance company or the like can perform maintenance for the walking assistance apparatus 23 at an appropriate maintenance timing by using the maintenance information provided from the information providing server 3.

Figure 6:
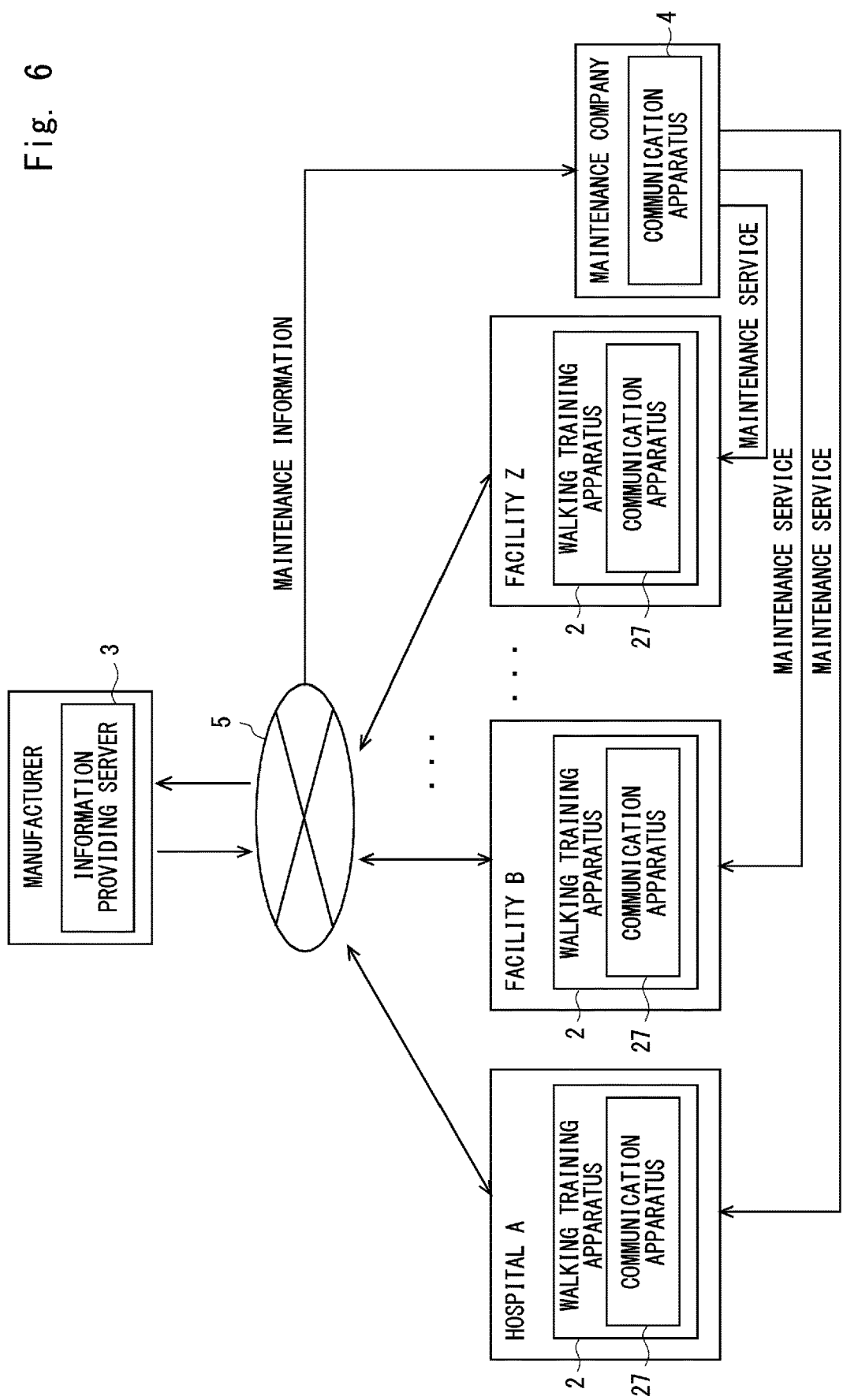
FIG. 6 is a block diagram showing a specific system configuration of a maintenance system according to an embodiment.

FIG. 6 is a block diagram showing a specific system configuration of the maintenance system according to this embodiment. The information providing server 3 is installed in, for example, a manufacturer or the like. The information providing server 3 installed in the manufacturer or the like, the walking training apparatus 2 installed in a hospital, a facility, or the like, and a communication apparatus 4 installed in a maintenance company are connected through, for example, a communication network 5 such as the Internet, so that they can perform data communication with each other.

Figure 7:
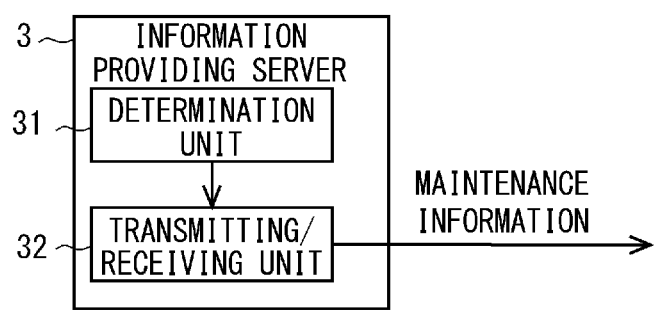
FIG. 7 is a block diagram showing a schematic system configuration of an information providing server according to an embodiment.

FIG. 7 is a block diagram showing a schematic system configuration of the information providing server according to this embodiment. The information providing server 3 includes a determination unit 31 that determines a timing for performing maintenance for the walking assistance apparatus 23, and a transmitting/receiving unit 32 that transmits/receives data.

The determination unit 31 is a specific example of the determination means. The determination unit 31 compares the integrated value of the number of times of walking transmitted from the communication apparatus 27 of the walking training apparatus 2 with a preset evaluation value (i.e., an evaluation value that is set in advance) for the durability of the walking assistance apparatus 23 (hereinafter referred to as the durability evaluation value), and determines a timing for performing maintenance for the walking assistance apparatus 23.

The timing for performing maintenance for the walking assistance apparatus 23 is, for example, a timing at which sensors such as the load sensors 240 and the angle sensor 239 provided in the walking assistance apparatus 23 are calibrated, or a timing at which consumable components of the walking assistance apparatus 23 such as the stopper pins 241 and the stopper shaft 242 are replaced.

The evaluation value for the durability of the walking assistance apparatus 23 is set in advance in the determination unit 31, and a user can arbitrarily change the set evaluation value. The evaluation value for the durability of the walking assistance apparatus 23 is, for example, a value that is experimentally obtained in advance by carrying out an endurance test or the like.

Assume that, for example, an endurance test of the walking assistance apparatus 23 is carried out under conditions that the dorsiflex moment load around the ankle joint part 235 is 60 Nm and the number of times of walking is 1 million, and the amount of wear of the stopper pin 241 reaches 0.3 mm and hence the stopper pin 241 needs to be replaced. In this case, the evaluation value for the durability of the walking assistance apparatus 23 is an integrated value of the dorsiflex moment load, which is 60 Nm, and the number of times of walking, which is 1 million.

Note that in the above description, the case in which the consumable components of the walking assistance apparatus 23 are the stopper pins 241 and the stopper shaft 242 of the adjustment mechanism 238. However, the consumable components are not limited to these components. The consumable component of the walking assistance apparatus 23 may be, for example, the load sensors 240 or a slipping prevention member(s) disposed on the sole of the sole frame 236.

When the determination unit 31 determines that the integrated value of the number of times of walking transmitted from the communication apparatus 27 of the walking training apparatus 2 is larger than a preset durability evaluation value for the walking assistance apparatus 23, it determines that it is a timing for performing maintenance for the associated component(s) of the walking assistance apparatus 23 at this stage. The determination unit 31 determines, for example, it is a timing for replacing the associated consumable component(s) of the associated walking assistance apparatus 23 at this stage.

The determination unit 31 may predict a timing for performing maintenance for the walking assistance apparatus 23 in the future by comparing the integrated value of the number of times of walking transmitted from the communication apparatus 27 of the walking training apparatus 2 with a preset durability evaluation value for the walking assistance apparatus 23. For example, the determination unit 31 calculates a difference between the integrated value of the number of times of walking and the durability evaluation value for the walking assistance apparatus 23. A relation between such differences and elapsed times is experimentally obtained in advance. The determination unit 31 predicts a timing for performing maintenance for the walking assistance apparatus 23 in the future based on the calculated difference and the relation between differences and elapsed times.

The transmitting/receiving unit 32 is a specific example of the second transmission means. The transmitting/receiving unit 32 transmits the maintenance information to the communication apparatus 4 or the like of a maintenance company that is registered in advance. The maintenance information is maintenance management information for recommending that the maintenance and management of the walking assistance apparatus 23 be necessary. The maintenance information includes at least a timing of maintenance for the walking assistance apparatus 23 at this stage or in the future determined by the determination unit 31 and information about the associated component(s) of the walking assistance apparatus 23.

A person in charge of the maintenance and management or the like in the maintenance company performs maintenance such as calibration of sensors of the corresponding walking assistance apparatus 23 and replacement of consumable components according to the maintenance timing received by the communication apparatus 4.

Note that as shown in FIG. 1, the information providing server 3 has, for example, a hardware configuration of a normal computer including a processor 3a such as a CPU (Central Processing Unit) or a GPU (Graphics Processing Unit), an internal memory 3b such as a RAM (Random Access Memory) or a ROM (Read Only Memory), a storage device 3c such as an HDD (Hard Disk Drive) or an SDD (Solid State Drive), an input/output I/F (Interface) 3d for connecting peripheral devices such as a display, and a communication I/F 3e for communicating with an apparatus located outside the information providing server.

By the information providing server 3, it is possible to implement each of the above-described functional components by, for example, having the processor 3a execute a program stored in the storage device 3c, the internal memory 3b, or the like while using the internal memory 3b.

Figure 8:
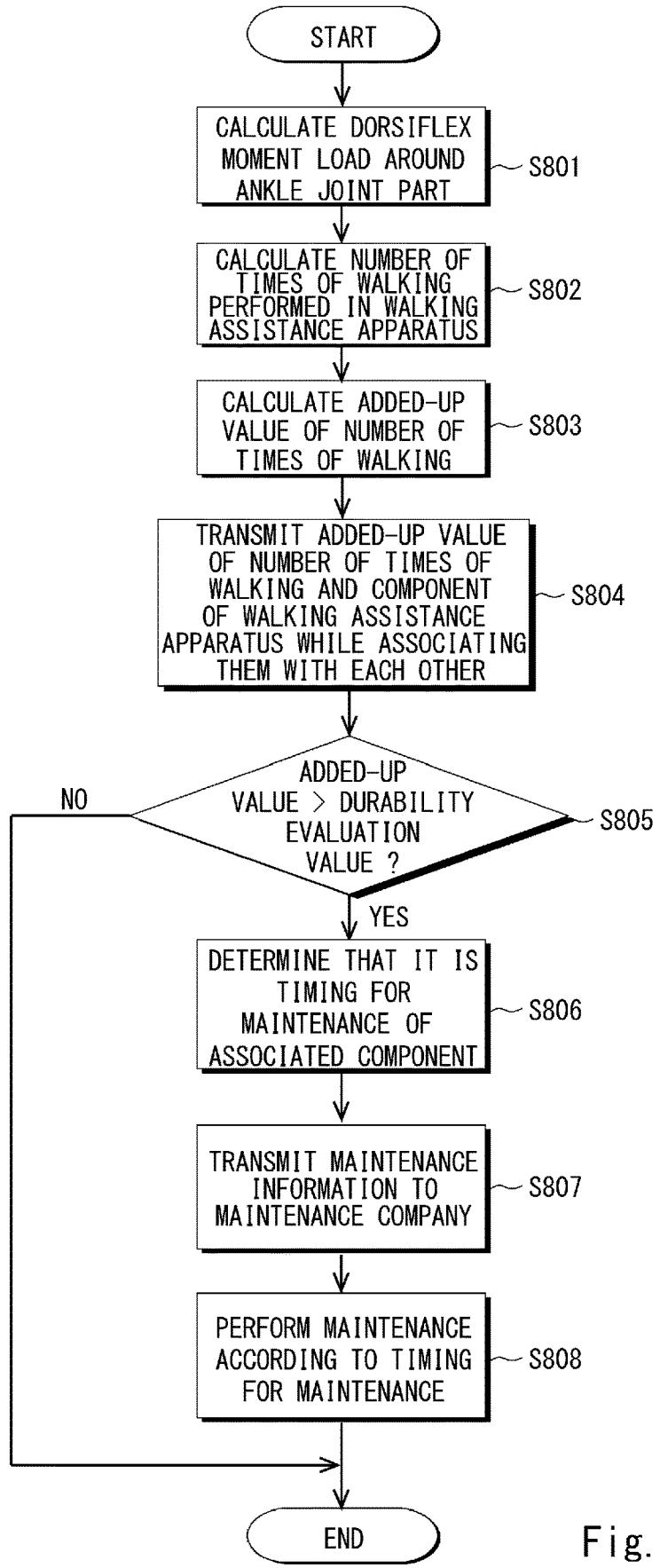
FIG. 8 is a flowchart showing a flow of a maintenance method according to an embodiment.

Next, a flow of a maintenance method according to this embodiment will be described. FIG. 8 is a flowchart showing a flow of a maintenance method according to this embodiment. The walking assistance apparatus 23 calculates a dorsiflex moment load around the ankle joint part 235 based on the loads detected by the respective load sensors 240 and the COP position (step S801).

The walking assistance apparatus 23 calculates the number N of times of walking performed in the walking assistance apparatus 240 based on the loads on the sole detected by the respective load sensors 23 (step S802).

The walking assistance apparatus 23 calculates an integrated value obtained by integrating the calculated the dorsiflex moment load around the ankle joint part and the number of times of walking (step S803).

The walking assistance apparatus 23 associates the calculated integrated value of the number of times of walking, as information about the number of times of walking, with a component of the walking assistance apparatus 23, and transmits the associated information to the communication apparatus 27 (step S804). The communication apparatus 27 transmits the received information in which the integrated value related to the number of times of walking is associated with the component of the walking assistance apparatus 23 to the information providing server 3.

The determination unit 31 of the information providing server 3 determines whether or not the integrated value related to the number of times of walking transmitted from the communication apparatus 27 is larger than a durability evaluation value for the walking assistance apparatus 23 (step S805).

When the determination unit 31 determines that the integrated value related to the number of times of walking is larger than the durability evaluation value (YES in step S805), it determines that it is a timing for performing maintenance for the associated component of the walking assistance apparatus 23 (step S806). On the other hand, when the determination unit 31 determines that the integrated value related to the number of times of walking is smaller than the durability evaluation value (NO in step S805), it finishes the series of processes.

The transmitting/receiving unit 32 transmits maintenance information including at least the timing of maintenance determined by the determination unit 31 and information about the associated component to the communication apparatus 4 of the maintenance company (step S807).

The maintenance company performs maintenance for the corresponding component of the walking assistance apparatus 23 according to the maintenance information transmitted from the transmitting/receiving unit 32 of the information providing server 3 (step S808).

As described above, in this embodiment, the determination unit 31 of the information providing server 3 compares the information about the number of times of walking or the time of walking transmitted from the communication apparatus 27 of the walking training apparatus 2 with the durability evaluation value for the walking assistance apparatus 23, and determines a timing for performing maintenance for the walking assistance apparatus 23. The transmitting/receiving unit 32 transmits maintenance information including at least the timing of maintenance determined by the determination unit 31 and information about the associated component of the walking assistance apparatus 23, which is the component to be maintained, to the communication apparatus 4 or the like of the maintenance company.

As a result, the maintenance company or the like can perform maintenance for the walking assistance apparatus 23 at an appropriate maintenance timing by using the maintenance information provided from the information providing server 3.

Second Embodiment

In this embodiment, the determination unit 31 of the information providing server 3 may change the evaluation value for the durability of the walking assistance apparatus 23 according to the position(s) of the stopper pin(s) 241 of the adjustment mechanism 238 of the walking assistance apparatus 23.

The movable range of the ankle joint part 235 is adjusted to, for example, 4°, 6°, 8°, . . . by the position of the stopper pin 241 of the adjustment mechanism 238. Further, the amounts of the wear of the stopper pin(s) 241 and the stopper shaft 242 change depending on the movable range of the ankle joint part 235. Therefore, it is possible to determine the timing of maintenance for the walking assistance apparatus 23 more accurately by changing the evaluation value for the durability of the walking assistance apparatus 23 according to the position of the stopper pin 241 of the adjustment mechanism 238.

For example, an endurance test is performed at each position of the stopper pin 241 of the adjustment mechanism 238, and the durability evaluation value is experimentally determined from the results of the tests and set in the determination unit 31. The determination unit 31 specifies the position of the stopper pin 241 of the adjustment mechanism 238 based on information that is input before a walking training is performed, and sets a durability evaluation value corresponding to the specified position of the stopper pin 241. The determination unit 31 compares the integrated value transmitted from the communication apparatus 27 with the set durability evaluation value and determines a timing for performing maintenance for the walking assistance apparatus 23.

Further, the amounts of the wear of the stopper pin(s) 241 and the stopper shaft 242 also change depending on which of the left and right legs the walking assistance apparatus 23 is attached to. Therefore, similarly to the change according to the position of the stopper pin 241 of the adjustment mechanism 238, the durability evaluation value for the walking assistance apparatus 23 may be changed according to which of the left and right sides the walking assistance apparatus 23 is attached to. The determination unit 31 specifies the side on which the walking assistance apparatus 23 is attached based on information that is input before a walking training is performed, and sets a durability evaluation value corresponding to the specified side.

Third Embodiment

Figure 9:
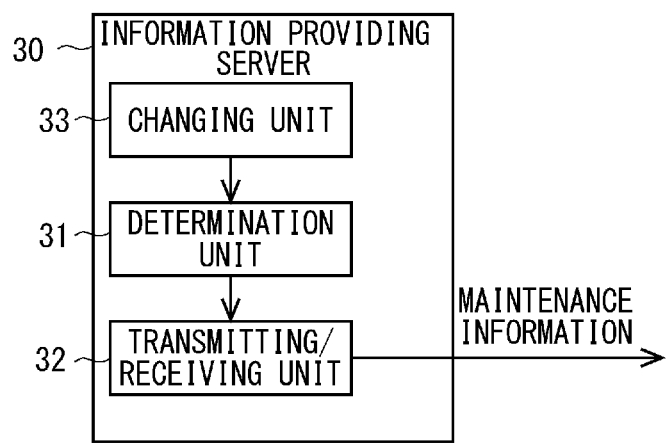
FIG. 9 is a block diagram showing a schematic system configuration of an information providing server according to an embodiment.

FIG. 9 is a block diagram showing a schematic system configuration of an information providing server according to this embodiment. An information providing server 30 according to this embodiment further includes a changing unit 33 that changes the durability evaluation value for the walking assistance apparatus 23. The changing unit 33 is a specific example of the changing means.

The durability evaluation value for the walking assistance apparatus 23 is set in advance in the determination unit 31, and a user can arbitrarily change the set durability evaluation value through the changing unit 33. In this way, it is possible to set (i.e., adjust) the durability evaluation value to an optimum value.

For example, there are possible cases in which although a consumable component of the walking assistance apparatus 23 is replaced according to the maintenance information provided from the information providing server 3, the amount of wear of the replaced (i.e., removed) consumable component is smaller than the amount of wear that is predicted based on the endurance test or the like and hence the consumable component can still be usable. In such a case, a user can change the durability evaluation value for the walking assistance apparatus 23 to a larger value through the changing unit 33. On the other hand, when the amount of wear of the replaced consumable is larger than the amount of wear predicted based on the endurance test or the like and hence the replacement time is later than the desirable timing, a user can change the durability evaluation value for the walking assistance apparatus 23 to a smaller value through the changing unit 33. In this way, it is possible to determine the timing of maintenance for the walking assistance apparatus 23 more accurately by adjusting the durability evaluation value for the walking assistance apparatus 23 according to the actual used-state of the walking assistance apparatus 23.

Fourth Embodiment

Figure 10:
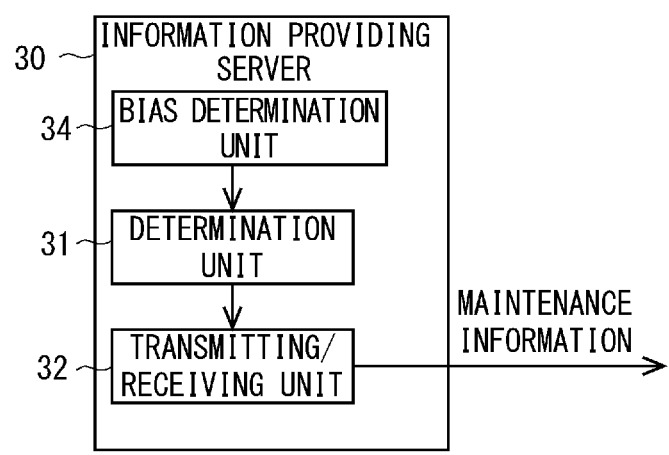
FIG. 10 is a block diagram showing a schematic system configuration of an information providing server according to an embodiment.

FIG. 10 is a block diagram showing a schematic system configuration of an information providing server according to this embodiment. The information providing server 30 according to this embodiment further includes a bias determination unit 34 that determines a direction of a bias of a load (hereinafter also referred to as a load bias direction) in walking performed by a trainee. The bias determination unit 34 is a specific example of the bias determination means.

The determination unit 31 sets a durability evaluation value according to the load bias direction in the walking of the trainee determined by the bias determination unit 34. As a result, an optimum durability evaluation value is set according to the habit of the trainee because of which the load is biased in his/her walking, thus making it possible to determine a timing for performing maintenance for the walking assistance apparatus 23 more accurately.

The bias determination unit 34 determines the load bias direction in the walking, such as being biased forward, backward, rightward, or leftward, based on information about at least one of the skeletal movement of the trainee, the COP position, and the knee joint angle, which is transmitted from the communication apparatus 27 of the walking training apparatus 2.

For example, when the COP position is closer to the toe, the bias determination unit 34 determines that the load bias direction in the walking is forward based on the COP position transmitted from the communication apparatus 27 of the walking training apparatus 2. Similarly, when the COP position is located on the right side, the bias determination unit 34 determines that the load bias direction in the walking is rightward based on the COP position transmitted from the communication apparatus 27 of the walking training apparatus 2.

The bias determination unit 34 may perform machine learning for data about the skeletal movement, the knee joint angle, and/or the like in advance by using a learning machine such as a neural network, and determine the load bias direction in the walking by using the result of the learning.

The durability evaluation value is experimentally obtained by performing a durability test or the like for each of the load bias directions. Durability evaluation values are set while being associated with respective load bias directions.

The determination unit 31 sets a durability evaluation value according to the load bias direction in the walking of the trainee determined by the bias determination unit 34. The determination unit 31 compares the set durability evaluation value with the integrated value of the number of times of walking transmitted from the communication apparatus 27 of the walking training apparatus 2, and determines a timing for performing maintenance for the walking assistance apparatus 23.

For example, the bias determination unit 34 determines that the load bias direction in the walking of the trainee is rightward based on the COP position transmitted from the communication apparatus 27 of the walking training apparatus 2. The determination unit 31 sets a durability evaluation value that is associated with the rightward load determined by the bias determination unit 34. The determination unit 31 compares the durability evaluation value for the rightward load with the integrated value of the number of times of walking transmitted from the communication apparatus 27 of the walking training apparatus 2, and determines a timing for performing maintenance for the walking assistance apparatus 23.

Several embodiments according to the present disclosure have been explained above. However, these embodiments are shown as examples but are not shown to limit the scope of the disclosure. These novel embodiments can be implemented in various forms. Further, their components/structures may be omitted, replaced, or modified without departing from the scope and spirit of the disclosure. These embodiments and their modifications are included in the scope and the spirit of the disclosure, and included in the scope equivalent to the invention specified in the claims.

In the present disclosure, for example, the processes shown in FIG. 8 can be implemented by having a processor execute a computer program.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.).

The program may be provided to a computer using any type of transitory computer readable media. Examples of transitory computer readable media include electric signals, optical signals, and electromagnetic waves. Transitory computer readable media can provide the program to a computer through a wired communication line (e.g. electric wires, and optical fibers) or a wireless communication line.

Note that each of the components constituting the maintenance system 1 according to the above-described embodiments can be implemented not only by a program(s), but also by dedicated hardware such as an ASIC (Application Specific Integrated Circuit) or an FPGA (Field-Programmable Gate Array).

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A maintenance system comprising:
a walking training apparatus comprising:
   a walking assistance apparatus configured to be attached to a leg of a trainee, and to assist the trainee in walking; and
   a first processor configured to transmit information about a number of times of walking or a time of walking performed in the walking assistance apparatus, the information being associated with a component of the walking assistance apparatus; and
   a server comprising a second processor configured to:
      compare the information about the number of times of the walking or the time of the walking transmitted from the first processor with a preset evaluation value for durability of the walking assistance apparatus, and determine a timing for performing maintenance for the walking assistance apparatus; and
      transmit maintenance information including the timing for performing maintenance determined by the second processor and information about the associated component of the walking assistance apparatus, the associated component being an object to be maintained, wherein
the first processor of the walking assistance apparatus is configured to:
   calculate a moment load around an ankle joint part of the walking assistance apparatus, and calculates an integrated value obtained by integrating the calculated moment load and the number of times of the walking or the time of the walking performed in the walking assistance apparatus; and
   transmit, as the information about the number of times of the walking or the time of the walking, the calculated integrated value while associating the calculated integrated value with the component of the walking assistance apparatus, and
the second processor is configured to compare the integrated value transmitted from the first processor with the preset evaluation value for the durability of the walking assistance apparatus, and determine the timing for performing the maintenance for the walking assistance apparatus.

2. The maintenance system according to claim 1, wherein the walking assistance apparatus comprises a thigh frame, a lower-leg frame connected to the thigh frame through a knee joint part, a sole frame connected to the lower-leg frame through the ankle joint part, a motor configured to rotationally drive the knee joint part, and an adjustment mechanism configured to adjust a movable range of the ankle joint part; and
the component of the walking assistance apparatus is configured to restrict the movable range of the ankle joint part in the adjustment mechanism.

3. The maintenance system according to claim 1, wherein the second processor is configured to change the presetevaluation value for the durability of the walking assistance apparatus.

4. A maintenance system comprising:
a walking training apparatus comprising:
   a walking assistance apparatus configured to be attached to a leg of a trainee, and to assist the trainee in walking; and
   a first processor configured to transmit information about the numbera number of times of walking or a time of walking performed in the walking assistance apparatus, the information being associated with a component of the walking assistance apparatus; and
   a server comprising a second processor configured to:
      compare the information about the number of times of the walking or the time of the walking transmitted from the first processor with a preset evaluation value for durability of the walking assistance apparatus, and determine a timing for performing maintenance for the walking assistance apparatus; and
      transmit maintenance information including the timing for performing maintenance determined by the second processor and information about the associated component of the walking assistance apparatus, the associated component being an object to be maintained, wherein
the first processor transmits, to the second processor, information about at least one of a skeletal movement of the trainee, a center of a load exerted on a sole frame, and a knee joint angle detected by a sensor provided in the walking training apparatus together with the information about the number of times of the walking or the time of the walking associated with the component of the walking assistance apparatus, and
the second processor is configured to:
   determine a direction of a bias of the load in the walking of the trainee based on the information about at least one of the skeletal movement of the trainee, the center of the load exerted on the sole frame, and the knee joint angle transmitted from the first processor;
   set the preset evaluation value for the durability according to the direction of the bias of the load in the walking of the trainee determined by the second processor;

compare the preset evaluation value for the durability with the information about the number of times of the walking or the time transmitted from the first processor; and determine the timing for performing the maintenance for the walking assistance apparatus.

5. A maintenance method comprising:

transmitting, to a server, information about a number of times of walking or a time of walking performed in a walking assistance apparatus, the information being associated with a component of the walking assistance apparatus, and the walking assistance apparatus being configured to be attached to a leg of a trainee, and to assist the trainee in walking;

comparing, by the server, the transmitted information about the number of times of the walking or the time of the walking with a preset evaluation value for durability of the walking assistance apparatus, and determining a timing for performing maintenance for the walking assistance apparatus;

transmitting, by the server, maintenance information including the determined timing for performing maintenance and information about the associated component of the walking assistance apparatus, the associated component being an object to be maintained;

calculating, by the walking assistance apparatus, a moment load around an ankle joint part of the walking assistance apparatus, and calculating an integrated value obtained by integrating the calculated moment load and the number of times of the walking or the time of the walking performed in the walking assistance apparatus;

transmitting, to the server, as the information about the number of times of the walking or the time of the walking, the calculated integrated value while associating the calculated integrated value with the component of the walking assistance apparatus; and comparing, by the server, the integrated value transmitted to the server with the preset evaluation value for the durability of the walking assistance apparatus, and determining the timing for performing the maintenance for the walking assistance apparatus.

6. A maintenance method comprising:

transmitting, to a server, information about a number of times of walking or a time of walking performed in a walking assistance apparatus is associated with a component of the walking assistance apparatus, the walking assistance apparatus being provided in a walking training apparatus and being configured to be attached to a leg of a trainee, and to assist the trainee in walking;

comparing, by the server, the transmitted information about the number of times of the walking or the time of the walking with a preset evaluation value for durability of the walking assistance apparatus, and determining a timing for performing maintenance for the walking assistance apparatus;

transmitting, by the server, maintenance information including the determined timing for performing maintenance and information about the associated component of the walking assistance apparatus, the associated component being an object to be maintained;

transmitting, to the server, information about at least one of a skeletal movement of the trainee, a center of a load exerted on a sole frame, and a knee joint angle detected by a sensor provided in the walking training apparatus together with the information about the number of times of the walking or the time of the walking associated with the component of the walking assistance apparatus;

determining, by the server, a direction of a bias of the load in the walking of the trainee based on the information about at least one of the skeletal movement of the trainee, the center of the load exerted on the sole frame, and the knee joint angle transmitted to the server;

setting, by the server, the preset evaluation value for the durability according to the direction of the bias of the load in the walking of the trainee determined by the server;

comparing, by the server, the preset evaluation value for the durability with the information about the number of times of the walking or the time transmitted to the server; and determining, by the server, the timing for performing the maintenance for the walking assistance apparatus.

* * * * *